United States Patent
Lefauconnier

(10) Patent No.: US 12,414,803 B2
(45) Date of Patent: Sep. 16, 2025

(54) SYSTEM FOR TIGHTENING AN ORTHOPEDIC SET SCREW AT TWO DIFFERENT TORQUE LEVELS

(71) Applicant: Neo Medical SA, La Villette (CH)

(72) Inventor: Vincent Lefauconnier, Brent (CH)

(73) Assignee: NEO MEDICAL SA, La Villette (CH)

( * ) Notice: Subject to any disclaimer, the term of this patent is extended or adjusted under 35 U.S.C. 154(b) by 798 days.

(21) Appl. No.: 17/439,834

(22) PCT Filed: Mar. 26, 2020

(86) PCT No.: PCT/IB2020/052857
§ 371 (c)(1),
(2) Date: Sep. 16, 2021

(87) PCT Pub. No.: WO2020/194227
PCT Pub. Date: Oct. 1, 2020

(65) Prior Publication Data
US 2022/0125489 A1    Apr. 28, 2022

(30) Foreign Application Priority Data

Mar. 26, 2019    (WO) .................. PCT/IB2019/052453

(51) Int. Cl.
A61B 17/70    (2006.01)
A61B 17/00    (2006.01)
(Continued)

(52) U.S. Cl.
CPC ........ *A61B 17/7091* (2013.01); *A61B 17/685* (2013.01); *A61B 17/708* (2013.01);
(Continued)

(58) Field of Classification Search
CPC ............ A61B 17/7091; A61B 17/7076; A61B 17/708; A61B 17/7082; A61B 90/03; A61B 2090/031
See application file for complete search history.

(56) References Cited

U.S. PATENT DOCUMENTS 2,826,107 A    3/1958  Glen
3,650,393 A    3/1972  Reiss
(Continued)

FOREIGN PATENT DOCUMENTS

CN    102026584 A    4/2011
CN    202446242      9/2012
(Continued)

OTHER PUBLICATIONS

Chapman, J. R., Harrington, R. M., Lee, K. M., Anderson, P. A., Tencer, A. F., & Kowalski, D. (1996). Factors affecting the pullout strength of cancellous bone screws. Journal of biomechanical engineering, 118(3), 391-398.
(Continued)

*Primary Examiner* — Eduardo C Robert
*Assistant Examiner* — Tara E Carter
(74) *Attorney, Agent, or Firm* — NIXON & VANDERHYE

(57) ABSTRACT

An orthopedic implant kit for tightening a set screw to a head of a pedicle screw for holding a spinal rod to the pedicle screw, the kit including a screw extender for holding the head of the pedicle screw, a set screw driver for engaging with the set screw to threadably tighten the set screw to the head of the pedicle screw, a first torque limiting mechanism for limiting a torque between the set screw driver and the screw extender to a first torque value or a first torque indication mechanism for indicating that the first torque has been reached, and a second torque limiting mechanism for
(Continued)

limiting a torque between the set screw driver and the screw extender to a second torque value, the second torque value being higher than the first torque value.

18 Claims, 9 Drawing Sheets

(51) Int. Cl.
  *A61B 17/68*  (2006.01)
  *A61B 17/88*  (2006.01)
  *A61B 90/00*  (2016.01)

(52) U.S. Cl.
  CPC ...... *A61B 17/7082* (2013.01); *A61B 17/8888* (2013.01); *A61B 90/03* (2016.02); *A61B 2017/00119* (2013.01); *A61B 2090/031* (2016.02)

(56) References Cited

U.S. PATENT DOCUMENTS

| | | |
|---|---|---|
| 4,244,434 A | 1/1981 | Wilson |
| 4,664,001 A | 5/1987 | Denman |
| 4,834,757 A | 5/1989 | Brantigan |
| 4,838,264 A | 6/1989 | Bremer |
| 5,048,381 A | 9/1991 | Allen |
| 5,129,388 A | 7/1992 | Vignaud |
| 5,347,894 A | 9/1994 | Fischer |
| 5,520,689 A | 5/1996 | Schlaepfer |
| 5,536,268 A | 7/1996 | Griss |
| 5,669,909 A | 9/1997 | Zdeblick |
| 5,720,751 A | 2/1998 | Jackson |
| 5,728,098 A | 3/1998 | Sherman |
| 5,734,113 A | 3/1998 | Vogt |
| 5,746,298 A | 5/1998 | Krivec |
| 5,797,918 A | 8/1998 | Mcguire |
| 5,882,350 A | 3/1999 | Ralph |
| 5,913,860 A | 6/1999 | Scholl |
| 5,984,923 A | 11/1999 | Breard |
| 6,056,753 A | 5/2000 | Jackson |
| 6,113,601 A | 9/2000 | Tatar |
| 6,183,472 B1 | 2/2001 | Lutz |
| 6,196,071 B1 | 3/2001 | Shomo |
| 6,258,090 B1 | 7/2001 | Jackson |
| 6,368,321 B1 | 4/2002 | Jackson |
| 6,371,968 B1 | 4/2002 | Kogasaka et al. |
| 6,398,552 B2 | 6/2002 | Rogers |
| 6,423,064 B1 | 7/2002 | Kluger |
| 6,454,768 B1 | 9/2002 | Jackson |
| 6,640,674 B1 | 11/2003 | Rinner |
| 6,644,087 B1 | 11/2003 | Ralph |
| 6,648,888 B1 | 11/2003 | Shluzas |
| 6,660,004 B2 | 12/2003 | Barker |
| 6,716,214 B1 | 4/2004 | Jackson |
| 6,740,086 B2 | 5/2004 | Richelsoph |
| 6,743,231 B1 | 6/2004 | Gray |
| 6,928,885 B1 | 8/2005 | Shiao |
| 7,066,937 B2 | 6/2006 | Shluzas |
| 7,160,300 B2 | 1/2007 | Jackson |
| 7,179,225 B2 | 2/2007 | Shluzas et al. |
| 7,197,968 B2 | 4/2007 | Bubel |
| 7,250,052 B2 | 7/2007 | Landry et al. |
| 7,491,168 B2 | 2/2009 | Raymond et al. |
| 7,520,879 B2 | 4/2009 | Justis |
| 7,527,638 B2 | 5/2009 | Anderson |
| 7,588,575 B2 | 9/2009 | Colleran |
| 7,604,655 B2 | 10/2009 | Warnick |
| 7,618,442 B2 | 11/2009 | Spitler |
| 7,651,502 B2 | 1/2010 | Jackson |
| 7,666,189 B2 | 2/2010 | Gerber et al. |
| 7,691,129 B2 | 4/2010 | Felix |
| 7,691,132 B2 | 4/2010 | Landry |
| 7,744,629 B2 | 6/2010 | Hestad et al. |
| 7,749,232 B2 | 7/2010 | Salerni |
| 7,806,026 B2 | 10/2010 | Gauthier |
| 7,811,288 B2 | 10/2010 | Jones |
| 7,842,044 B2 | 11/2010 | Runco et al. |
| 7,862,587 B2 | 1/2011 | Jackson |
| 7,892,238 B2 | 2/2011 | DiPoto et al. |
| 7,892,259 B2 | 2/2011 | Biedermann et al. |
| 7,922,725 B2 | 4/2011 | Darst Rice et al. |
| 7,931,673 B2 | 4/2011 | Hestad et al. |
| 7,938,046 B2 | 5/2011 | Nino |
| 7,951,172 B2 | 5/2011 | Chao |
| 7,967,821 B2 | 6/2011 | Sicvol et al. |
| 8,016,832 B2 | 9/2011 | Vonwiller et al. |
| 8,016,862 B2 | 9/2011 | Felix et al. |
| 8,028,608 B2 | 10/2011 | Sixto, Jr. |
| 8,034,086 B2 | 10/2011 | Iott |
| 8,052,724 B2 | 11/2011 | Jackson |
| 8,088,163 B1 | 1/2012 | Kleiner |
| 8,114,085 B2 | 2/2012 | Von Jako |
| 8,128,667 B2 | 3/2012 | Jackson |
| 8,137,356 B2 | 3/2012 | Hestad et al. |
| 8,152,810 B2 | 4/2012 | Jackson |
| 8,167,911 B2 | 5/2012 | Shluzas et al. |
| 8,197,519 B2 | 6/2012 | Schlaepfer |
| 8,225,679 B2 | 7/2012 | Flaherty |
| 8,246,665 B2 | 8/2012 | Butler et al. |
| 8,262,662 B2 | 9/2012 | Beardsley |
| 8,262,704 B2 | 9/2012 | Matthis et al. |
| 8,308,782 B2 | 11/2012 | Jackson |
| 8,317,796 B2 | 11/2012 | Stihl et al. |
| 8,366,747 B2 | 2/2013 | Shluzas |
| 8,372,121 B2 | 2/2013 | Capote |
| 8,382,805 B2 | 2/2013 | Wang et al. |
| 8,394,109 B2 | 3/2013 | Hutton et al. |
| 8,465,546 B2 | 6/2013 | Jodaitis |
| 8,469,960 B2 | 6/2013 | Hutton |
| 8,562,652 B2 | 10/2013 | Biedermann |
| 8,603,094 B2 | 12/2013 | Walker et al. |
| 8,603,145 B2 | 12/2013 | Forton |
| 8,608,746 B2 | 12/2013 | Kolb et al. |
| 8,617,218 B2 | 12/2013 | Justis et al. |
| 8,636,783 B2 | 1/2014 | Crall et al. |
| D715,611 S | 10/2014 | Stamm |
| 8,870,878 B2 | 10/2014 | Gorek |
| 8,876,868 B2 | 11/2014 | Jackson |
| 9,050,139 B2 | 6/2015 | Jackson |
| 9,066,758 B2 | 6/2015 | Justis et al. |
| 9,066,761 B2 | 6/2015 | McBride et al. |
| 9,101,401 B2 | 8/2015 | Dalton et al. |
| 9,138,261 B2 | 9/2015 | Di Lauro et al. |
| 9,204,909 B2 | 12/2015 | Rezach et al. |
| 9,211,143 B2 | 12/2015 | Barry |
| 9,211,149 B2 | 12/2015 | Hoefer et al. |
| 9,326,798 B2 | 5/2016 | Kolb et al. |
| 9,408,649 B2 | 8/2016 | Felix et al. |
| 9,492,209 B2 | 11/2016 | Biedermann et al. |
| 9,526,537 B2 | 12/2016 | Meyer et al. |
| 9,585,702 B2 | 3/2017 | Hutton |
| 9,655,653 B2 | 5/2017 | Lindner et al. |
| 9,707,019 B2 | 7/2017 | Miller et al. |
| 9,924,982 B2 | 3/2018 | Jackson |
| 9,962,197 B2 | 5/2018 | Dandaniopoulos et al. |
| 9,968,378 B1 | 5/2018 | Johnson |
| 10,034,701 B2 | 7/2018 | Adamiec |
| 10,058,355 B2 | 8/2018 | Beyer |
| 2003/0114860 A1* | 6/2003 | Cavagna ............ A61B 17/8875 606/104 |
| 2004/0144149 A1 | 7/2004 | Strippgen |
| 2005/0131408 A1 | 6/2005 | Sicvol |
| 2005/0192570 A1 | 9/2005 | Jackson |
| 2005/0192579 A1 | 9/2005 | Jackson |
| 2005/0240197 A1 | 10/2005 | Kmiec, Jr. |
| 2006/0025771 A1 | 2/2006 | Jackson |
| 2006/0036244 A1 | 2/2006 | Spitler et al. |
| 2006/0089644 A1 | 4/2006 | Felix |
| 2006/0111712 A1 | 5/2006 | Jackson |
| 2006/0111715 A1 | 5/2006 | Jackson |
| 2006/0217719 A1 | 9/2006 | Albert |
| 2006/0241599 A1 | 10/2006 | Konieczynski |
| 2006/0276789 A1 | 12/2006 | Jackson |

(56) References Cited

U.S. PATENT DOCUMENTS

| | | |
|---|---|---|
| 2007/0078460 A1 | 4/2007 | Frigg |
| 2007/0106123 A1 | 5/2007 | Gorek |
| 2007/0233091 A1 | 10/2007 | Naifeh |
| 2007/0239159 A1 | 10/2007 | Altarac |
| 2007/0261868 A1 | 11/2007 | Gross |
| 2007/0270866 A1 | 11/2007 | Von Jako |
| 2008/0039839 A1 | 2/2008 | Songer |
| 2008/0119852 A1 | 5/2008 | Dalton |
| 2008/0147129 A1 | 6/2008 | Biedermann |
| 2008/0154279 A1 | 6/2008 | Schumacher |
| 2008/0200918 A1 | 8/2008 | Spitler |
| 2008/0243189 A1 | 10/2008 | Purcell |
| 2008/0262318 A1 | 10/2008 | Gorek |
| 2008/0294172 A1 | 11/2008 | Baumgart |
| 2008/0294203 A1 | 11/2008 | Kovach |
| 2009/0171391 A1 | 7/2009 | Hutton |
| 2009/0204159 A1 | 8/2009 | Justis |
| 2009/0221879 A1 | 9/2009 | Gorek |
| 2009/0222045 A1 | 9/2009 | Gorek |
| 2009/0281571 A1 | 11/2009 | Weaver |
| 2010/0152785 A1 | 6/2010 | Forton et al. |
| 2010/0292742 A1* | 11/2010 | Stad ............... A61B 17/7091 606/279 |
| 2010/0312103 A1 | 12/2010 | Gorek |
| 2011/0040328 A1 | 2/2011 | Miller et al. |
| 2011/0106179 A1 | 5/2011 | Prevost |
| 2011/0166606 A1 | 7/2011 | Stihl et al. |
| 2011/0172718 A1 | 7/2011 | Felix et al. |
| 2011/0245883 A1 | 10/2011 | Dall |
| 2011/0263945 A1 | 10/2011 | Peterson et al. |
| 2011/0313460 A1 | 12/2011 | McLean et al. |
| 2011/0319896 A1 | 12/2011 | Papenfuss |
| 2012/0031792 A1 | 2/2012 | Petit |
| 2012/0186411 A1 | 7/2012 | Lodahi |
| 2013/0012999 A1 | 1/2013 | Petit |
| 2013/0023941 A1 | 1/2013 | Jackson et al. |
| 2013/0096624 A1 | 4/2013 | Di Lauro et al. |
| 2014/0031828 A1 | 1/2014 | Patel |
| 2014/0052187 A1 | 2/2014 | McBride et al. |
| 2014/0100613 A1 | 4/2014 | Iott et al. |
| 2014/0128878 A1 | 5/2014 | O'neil |
| 2014/0171955 A1 | 6/2014 | Smith |
| 2014/0277203 A1* | 9/2014 | Atoulikian ............ B25B 17/02 606/86 A |
| 2015/0066042 A1 | 3/2015 | Cummins et al. |
| 2015/0265322 A1 | 9/2015 | Jackson |
| 2015/0351810 A1 | 12/2015 | Lindner et al. |
| 2016/0089186 A1 | 3/2016 | Beyer |
| 2016/0166304 A1 | 6/2016 | Stad |
| 2016/0287294 A1 | 10/2016 | Kubo |
| 2016/0346026 A1 | 12/2016 | Bootwala |
| 2016/0374825 A1 | 12/2016 | Kleiner |
| 2017/0095272 A1 | 4/2017 | Hutton et al. |
| 2017/0143384 A1 | 5/2017 | Hutton et al. |
| 2017/0181774 A1 | 6/2017 | Cahill |
| 2017/0181775 A1 | 6/2017 | Jackson |
| 2017/0189082 A1 | 7/2017 | Petit |
| 2017/0348037 A1 | 12/2017 | Sexson |
| 2018/0214186 A1 | 8/2018 | Beyer |
| 2018/0289397 A1 | 10/2018 | Buttermann |

FOREIGN PATENT DOCUMENTS

| | | |
|---|---|---|
| CN | 202497225 U | 10/2012 |
| CN | 203777040 | 8/2014 |
| CN | 203777040 U | 8/2014 |
| CN | 105662662 A | 6/2016 |
| EP | 1726264 A1 | 11/2006 |
| EP | 1854587 A2 | 11/2007 |
| EP | 1994892 A1 | 11/2008 |
| EP | 1994902 A2 | 11/2008 |
| EP | 2198793 A2 | 6/2010 |
| EP | 2283787 | 2/2011 |
| EP | 2283787 A1 | 2/2011 |
| EP | 2522287 | 11/2012 |
| EP | 2522287 A1 | 11/2012 |
| EP | 2692304 A1 | 2/2014 |
| JP | 2007283101 | 11/2007 |
| JP | 2011500267 | 1/2011 |
| JP | 2011500267 A | 1/2011 |
| JP | 2012507316 | 3/2012 |
| JP | 2013515580 | 5/2013 |
| TW | M273326 U | 8/2005 |
| WO | 9819616 A1 | 5/1998 |
| WO | WO 9819616 | 5/1998 |
| WO | 2005060837 A2 | 7/2005 |
| WO | WO 2005060837 | 7/2005 |
| WO | 2006045089 A2 | 4/2006 |
| WO | WO 2006045089 | 4/2006 |
| WO | 2006091863 A2 | 8/2006 |
| WO | WO 2006091863 | 8/2006 |
| WO | 2006130179 A2 | 12/2006 |
| WO | WO 2006130179 | 12/2006 |
| WO | 2007092870 A2 | 8/2007 |
| WO | WO 2007092870 | 8/2007 |
| WO | 2007117366 A2 | 10/2007 |
| WO | WO 2007117366 | 10/2007 |
| WO | 2008097974 A2 | 8/2008 |
| WO | WO 2008097974 | 8/2008 |
| WO | 2009055026 A1 | 4/2009 |
| WO | 2009055034 A1 | 4/2009 |
| WO | WO 2009055026 | 4/2009 |
| WO | WO 2009055034 | 4/2009 |
| WO | 2009114422 A2 | 9/2009 |
| WO | WO 2009114422 | 9/2009 |
| WO | 2009137246 A1 | 11/2009 |
| WO | WO 2009137246 | 11/2009 |
| WO | WO 2010052462 | 5/2010 |
| WO | WO 2011080426 | 7/2011 |

OTHER PUBLICATIONS

International Search Report mailed on Aug. 21, 2020 for Application N° PCT/IB2020/052857.

Paik, H., Kang, D. G., Lehman Jr, R. A., Gaume, R. E., Ambati, D. V., & Dmitriev, A. E. (2013). The biomechanical consequences of rod reduction on pedicle screws: should it be avoided?. The Spine Journal, 13(11), 1617-1626.

Written Opinion of the ISA mailed on Aug. 21, 2020 for Application N° PCT/IB2020/052857.

* cited by examiner

SYSTEM FOR TIGHTENING AN ORTHOPEDIC SET SCREW AT TWO DIFFERENT TORQUE LEVELS

CROSS-REFERENCE TO RELATED APPLICATIONS

The present patent application claims priority to the International Patent Application with the Serial No. PCT/B2019/052453 that was filed on Mar. 26, 2019, the contents thereof herewith incorporated by reference in its entirety.

The present application is a United States national stage application of International patent application PCT/IB2020/052857 filed on Mar. 26, 2020 designating the United States, and claims foreign priority to International patent application PCT/IB2019/052453 filed on Mar. 26, 2019, the contents of both documents being herewith incorporated by reference in their entirety.

FIELD OF THE INVENTION

The present invention relates to orthopedics and more precisely to orthopedic tools and systems including pedicle screws, rods and corresponding set screws. The invention also relates to instruments which are used for manipulating these elements, and methods of using these elements, to apply a torque to a set screw.

BACKGROUND

In the field of orthopedics and implant tools and systems for orthopedic surgery, more specifically spinal fusion surgery for a spinal column, set screws are used to push down and attach a rod-type or bar-type device to a head of a pedicle screw. The process of pushing down the spinal rod towards and into the head of pedicle screw is also called rod reduction. Before attaching the rod to the head of the pedicle screw, the pedicle screw is attached to a vertebrae with a bone anchor, threaded bone-engaging part or bone screw for fastening the pedicle screw to the vertebrae of a patient or living being. For this purpose, as an example, for several adjacent vertebrae for vertebrae fusion, for each vertebra a pedicle screw is attached thereto, and thereafter, several pedicle screws are mechanically fastened towards each other by the use of the rod that is placed in a groove or U-shaped opening that is formed by the pedicle screw head, forming a row of pedicle screws along the spine. This allows to provide for the mechanical support needed for spinal stabilization for spinal fusion in a patient or living being.

For example, U.S. Pat. No. 10,058,355, this reference herewith incorporated by reference in its entirety, describes an orthopedic implant kit that provides for a pedicle screw, a corresponding set screw, a rod, and the tools to operate these, including a screw extender for holding the pedicle screw, and a set screw driver for threadably tightening the set screw relative to screw head of pedicle screw. As another example, U.S. Pat. No. 8,795,283, this reference herewith incorporated by reference in its entirety, describes another type of kit orthopedic surgery system for surgical intervention for spinal stabilization, including pedicle screw with a head for receiving a rod, and tools necessary for the surgical intervention. In yet another example, U.S. Pat. No. 8,262,662, this reference herewith incorporated by reference in its entirety, provides for a system and method for delivering a spinal connector spinal anchor sites in a spinal column. In one embodiment, a spinal implant and access device is provided that includes a U-shaped receiver member, a bone-engaging member, an extension member, a spinal rod, and a set screw.

Similar orthopedic spinal surgery concepts, tools and devices have been proposed as discussed above, for attaching a rod to a pedicle screw via a set screw, for example U.S. Pat. Nos. 5,129,388, 5,520,689, 5,536,268, 5,720,751, 5,984,923, 6,056,753, 6,183,472, 6,258,090, 6,454,768, 6,648,888, 6,740,086, 7,618,442, 8,308,782, 8,876,868, U.S. Patent Publication No. 2006/0025771, and U.S. Patent Publication No. 2018/0289397, all of these references herewith incorporated by reference in its entirety.

However, the state of the art tools still present specific problems when a surgeon or operator of the spinal surgery tools needs to attach the rod to the pedicle screw by means of the set screw, specifically to find the right amount of torque that needs to be applied to the set screw under different circumstances. Therefore, despite all of the solutions currently proposed in the state of the art related spinal surgery tools, strongly improved methods, systems and devices for spinal surgery are strongly desired.

SUMMARY

According to one aspect of the present invention, a method for tightening a set screw to a head of a pedicle screw for holding a spinal rod is provided, the head of the pedicle screw having a groove that accommodates the spinal rod. Preferably, the method includes the steps of threadably engaging a set screw to the head of the pedicle screw, attaching a set screw driver to the set screw, first tightening the set screw to the head of the pedicle screw and the spinal rod with a first torque that is limited by a first torque limiting mechanism associated with the set screw driver, or by a first torque indication mechanism for indicating that the first torque has been reached, and second tightening the set screw to the head of the pedicle screw and the spinal rod with a second torque that is higher than the first torque by a second torque limiting mechanism associated with the set screw driver.

According to another aspect of the present invention, an orthopedic implant kit for tightening a set screw to a head of a pedicle screw for holding a spinal rod to the pedicle screw is provided. Preferably, the orthopedic implant kit includes a screw extender for holding the head of the pedicle screw, a set screw driver for engaging with the set screw to threadably tighten the set screw to the head of the pedicle screw, a handle for turning the set screw driver relative to the screw extender, a first torque limiting mechanism for limiting a torque between the set screw driver and the screw extender to a first torque value, or a first torque indication mechanism for indicating that the first torque has been reached, and a second torque limiting mechanism for limiting a torque between the set screw driver and the screw extender to a second torque value, the second torque value being higher than the first torque value.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

FIG. 1E shows a separate torque limiting mechanism 327 that can be operatively placed between upper shaft 8 or proximal end of set screw driver 26 and the handle 25;

Herein, identical reference numerals are used, where possible, to designate identical elements that are common to the figures. Also, the images are simplified for illustration purposes and may not be depicted to scale.

DETAILED DESCRIPTION OF THE SEVERAL EMBODIMENTS

Figure 1A:
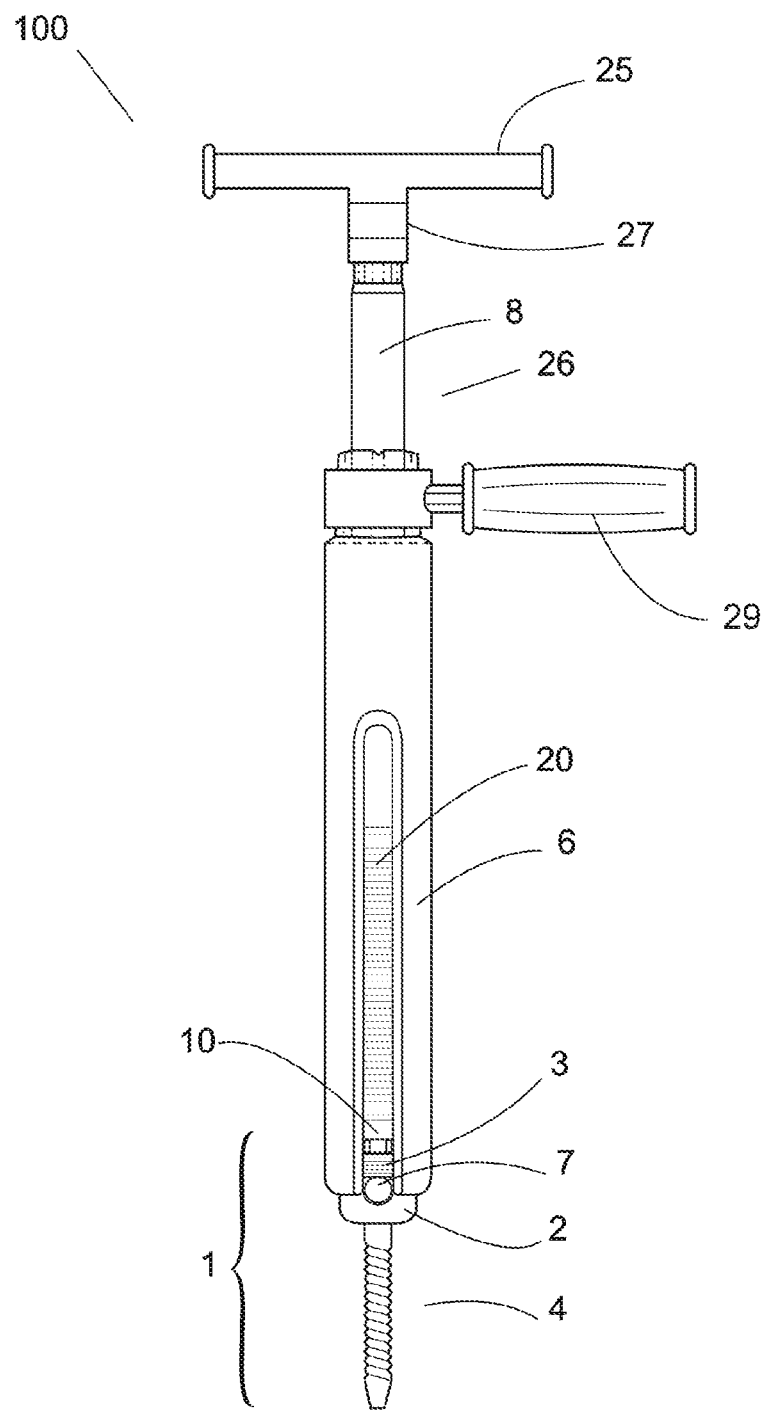
FIGS. 1A-1E show different side views of elements of an orthopedic implant kit 100 having a first torque limiting or indicating feature, and a second torque limiting feature, with FIG. 1A showing a side cross-sectional view of the orthopedic tool kit 100 with pedicle screw 1, screw head 2, set screw or fastener 3, spinal rod 7, screw extender 6, set screw driver 26, first torque handle 25, and second counter-torque handle 29, FIG. 1B showing the same view of FIG. 1A with some cross-sectional views inside set screw driver 26, screw extender 6, and first torque handle 25, FIG. 1C showing a handle 125 with a torque indication mechanism 127, for example a torque scale, FIG. 1D showing a simple handle 225, with or without ratcheting mechanism.
Figure 1B:
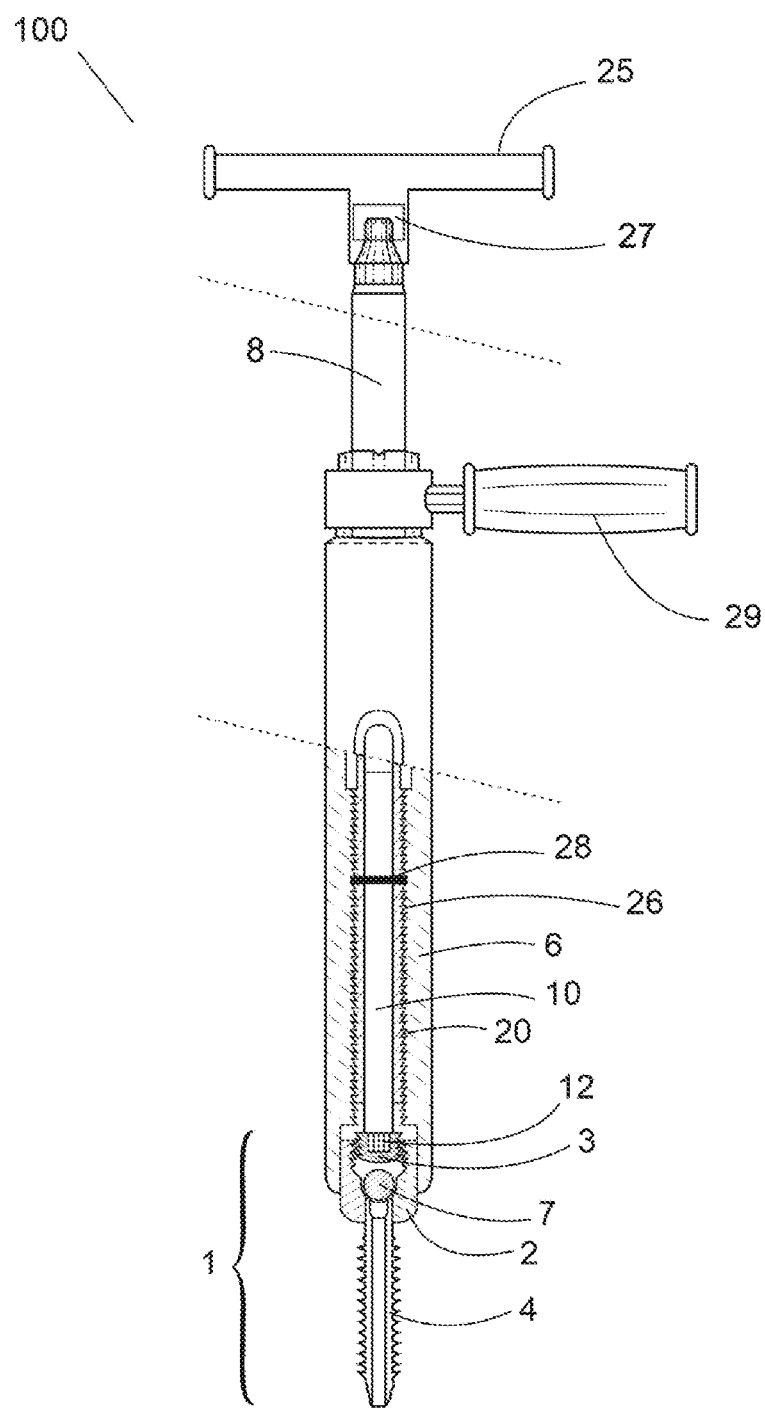

According to one embodiment, as exemplarily shown in FIGS. 1A and 1B, an orthopedic implant kit, instrument kit, tool kit, or system 100 is provided, including a handle 25, a first torque limiting or indicating device 27, a set screw driver 8 that may include the second torque limiting device 28 that can be turned by handle 25, a second counter handle 29, a screw extender 6, the second counter handle 29 engaging with set screw driver 6, a set screw 3, a pedicle screw 1 with screw head 2 and bone anchor or threaded part 4, and a spinal rod 7. In the variant shown, first torque limiting mechanism or device 27 that limits an application of a torque to a first torque level T1 is an integral part or is affixed or otherwise operatively connected to a first handle 25, for example a T-handle, that is used to tightening a set screw 3 to a head 2 of the pedicle screw 1 via a set screw driver 26. The first torque level T1 is a torque that is applied to set screw 3 relative to a head 2 of pedicle screw 1, for example when set screw 3 is threadably engaged with a head 2 of a pedicle screw 1, and also by abutting or otherwise fastening a spinal rod 7 to head 2 of pedicle screw 1. First handle 25 can have the torque limiting mechanism device 27 can be removably attached to the set screw driver 26 for tightening the set screw 3 can be used as the first torque limiting mechanism, for example a handle 25 that attaches to an end of upper shaft 8, proximal end, or another part of set screw driver 26. Such handles with a torque limiting mechanism 27 for tightening a screw are described in U.S. Pat. Nos. 2,826,107, 4,244,434, 4,838,264, 5,347,894, 5,746,298, 6,640,674, 7,197,968, 7,938,046, 8,028,608, and 10,034,701, these reference herewith incorporated by reference in their entirety. A screw extender 6 or screw head holder is affixed to screw head 2 of pedicle screw 1, and a counter handle 29 is in turn attached to screw extender 6 for counter torque purposes, when tightening set screw 3 relative to screw head 2.

The application of the right amount of torque to a set screw 3 that is being tightened against a spinal rod 7 held by a head 2 of a pedicle screw 1 is important and depends on the specific circumstance during the orthopedic surgical operation. Also, an angulation of the tightening of set screw 3 is also an important aspect, which can translate into higher amount of torque which then can be transmitted to the surrounding tissues creating risk of screw loosening, implant breakage and/or risk of adjacent segment disease. The present embodiments describe a solution to the fact that a user, operator or surgeon needs to apply different levels of torque during the surgery, and provides for a mechanism that simplifies the task substantially. See for example the publications Chapman et al., "Factors Affecting the Pullout Strength of Cancellous Bone Screws," Journal of Biomechanical Engineering, ASME, Vol. 118, 391-398, 1996, and Paik et al. "The Biomechanical Consequences of Rod Reduction on Pedicle Screws: Should it be avoided?" The Spine Journal, Vol. 13, No. 11, pp. 1617-1626, 2013, these references herewith incorporated by reference in their entirety.

Figure 1C:
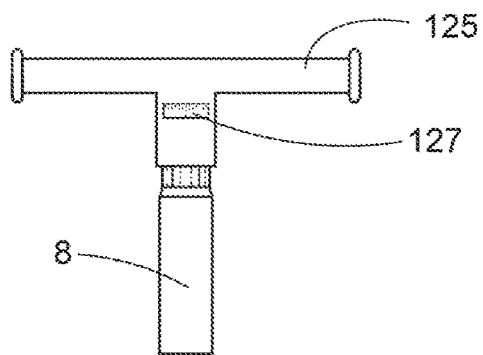
Figure 1D:
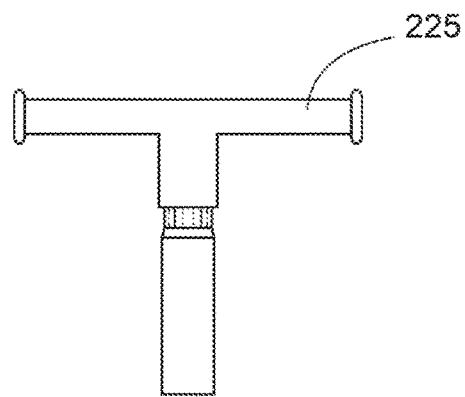

In a variant, as shown in FIG. 1C, it is possible that a first handle 125 is used having a torque indication mechanism 127, instead of a mechanism 27 that physically limits the applicable torque to set screw 3, but makes some type of indication that the first torque level T1 has been reached, for example but not limited to a visual, haptic, tactile, vibratory, mechanical, audible noise for example a clicking noise or beep, or combination thereof, or other type of feedback that can be seen, heard, or sensed by the user or operator, or any combination of these features. This can be done with or without any device that actually limits the physical torque applied to set screw 3. For example, a first handle 125 can be used that incorporates a torque measurement mechanism that is associated with a torque indicator, scale, or gauge 127. For example, handles 125, wrenches, screwdrivers, drivers, instruments, keys, tools, or sockets that are based on the operational principles as described in U.S. Pat. Nos. 4,664,001, 5,048,381, 5,734,113, 6,196,071, 6,398,552, 6,928,885, 7,806,026, 8,225,679, and D715,611 and similar mechanisms can be used for the purpose of tightening set screw 3 via set screw driver 26, and simultaneously alerting or otherwise indicating the user or operator that a first torque level T1 has been reached, all of these references herewith incorporated by reference in their entirety.

First torque level T1 can be specifically designed for the application to blockable poly-axial screws, for example poly-axial pedicle screws that can be blocked by a pressure caused by the tightening of the spinal rod 7 via set screw 3, as shown exemplarily in U.S. Pat. Nos. 5,882,350, 6,113,601, and 6,660,004 these references herewith incorporated by reference in their entirety. Another variant is the Medtronic™ CD Horizon Solera pedicle screw system that allows for such blocking, having a blocking ring or seat that urges against the spherical head of pedicle screw. In this variant, first torque level between set screw 3 and screw head 2 is such that rotational motions of spinal rod 7 around its own axis are blocked, when tightened to torque level T1 within screw head 2 of pedicle screw 1, for example such that a surgeon, user, or operator cannot turn or otherwise rotate rod 7 within groove of screw head. However, with torque level T1, the pedicle screw 1 still maintains its polyaxiality, as the pressure onto upper or side surfaces of spherical part of bone anchor 4 and the blocking ring or seat are not sufficient to block polyaxiality Preferably, first torque level T1 is approximatively in a range between 0.7 Nm and 2.1 Nm, more preferably about 1.4 Nm.

Next, a second torque limiting mechanism 28 that limits an application of a torque to a second torque value or level T2 to the set screw 3 relative to the head 2 of pedicle screw 1 can be integrated in to the set screw driver 26, as shown in U.S. Pat. No. 10,058,355, this references incorporated by reference in its entirety. For example, as shown in the cross-sectional view of FIG. 1B, set screw driver 26 includes an upper shaft 8 which end can engage with a first handle 25, 125, 225, for example by different mechanical connection types, with the lower shaft 20 being hollow for accommodating a torque driver 10. An engagement tool 12 of torque driver 10 can protrude from lower face or distal part of lower shaft 20, to be able to engage with set screw 3 for threadable tightening relative to screw head 2, with a screw engagement mechanism 12. Torque driver 10 and lower shaft 20 are blocked relative to each other by a breakable pin 28 that traverses at least a portion of both lower shaft 20 and torque driver 10, forming a second torque limiting mechanism 28 that mechanically limits the amount of torque that can be applied to set screw 3 via handle 125 to the second torque level T2, relative to screw head 2 of pedicle screw 1. In the variant shown, torque driver 10 is formed by an inner bolt, rod, or shaft that is surrounded at a lower section by the lower shaft 20.

The second torque level T2 is the final torque that will be applied to rod 7 and screw head 2 via set screw 3, and is substantially higher than the first torque level. Because the second torque level is the final level that will be applied to the set screw 3, the torque limiting mechanism can be irreversible or can be such that no higher torque levels can be applied to set screw 3. Preferably, the second torque level T2 is approximatively in a range between 8 Nm and 12 Nm, more preferably about 10 Nm.

Set screw driver 26 has an outer threading that can threadably engage with an inner threading of screw extender, having the same thread pitch as the threading of the set screw. This allows the user or operator to place set screw 3 onto the front portion of torque driver 10 of set screw driver 26, and then threadably engage with inner threading of screw extender 6, to turn or rotate set screw 3 together with set screw driver 26 down through the screw extender, until set screw 3 makes contact and threadably engages with inner threading of head 2 of pedicle screw 1. When set screw 3 is threadably affixed within the head 2 and set screw driver 26 is continued to be rotated or turned by a handle 125, 225, once frontal face FF of the set screw 3 touches spinal rod 7, the torque increases, up to a point where the pin 28 breaks. Pin 28 is designed and dimensioned to withhold a torque up to the second torque level T2, and will break upon exceeding the second torque level T2. Once the pin 28 is broken, a further rotation of set screw driver 26 has therefore no more effect on the rotation and threadable engagement of set screw 3 within head 2 of pedicle screw 1, as torque driver 10 will not be rotated by set screw driver 26 anymore. In other words, set screw driver 26 can freely rotated without rotating torque driver 10. Therefore, when the second torque limiting mechanism 28, in the variant shown the breakable pin, is activated or in force, i.e. the second torque level T2 has been reached and pin 28 is broken, when user or operator rotates set screw driver 26 by a holding handle 125, set screw driver 26 will threadably be advancing downwards towards the set screw 3, without turning set screw 3. In turn, pedicle screw 1 will be progressively pushed away and released from screw extender 6. Second handle 29 is removably attached to screw extender 6, so that the user or operator can tighten set screw 3 into head 2 of pedicle screw 1 with one hand, whilst holding head 2 of pedicle screw via screw extender 6 and second handle 29. This operational principle of second torque limiting mechanism 28 that is integrated to set screw driver 26 is also shown with FIGS. 13A-13C, 14, and 15 of U.S. Pat. No. 10,058,355 that is herewith incorporated by reference in its entirety. It is also possible that the second torque limiting mechanism is combined with a torque indicating mechanism, or does not limit the torque to torque level T2, but only indicates it.

The first torque limiting mechanism 27 or the first torque indicating mechanism 127 are preferably designed such that the first torque level T1 is smaller than the second torque level T2 that is applied by the second torque limiting mechanism 28, for example by a factor that is bigger than five (5). This means that in case a first torque limiting mechanism 27 is used with handle 25, once the first torque level has been reached, the applicable torque to set screw 3 cannot be increased anymore by handle 25. Therefore, this requires that a user or operator to remove handle 25 from set screw driver 26, and replace handle 25 by placing another handle, for example handle 25 with a mechanism that limits the torque to a second, higher torque level T2, a handle 125 having only a torque indication mechanism 127 or another type of handle 225 with no torque limitation or indication to set screw driver 26, so that the second, higher level of torque can be applied to set screw 3, until the second torque level T2 is reached. In case handle 125 is used, the same handle can be used to apply the first level of torque T1 and the second level of torque T2, for example by having a scale showing the two different torque levels T1 and T2.

Figure 1E:
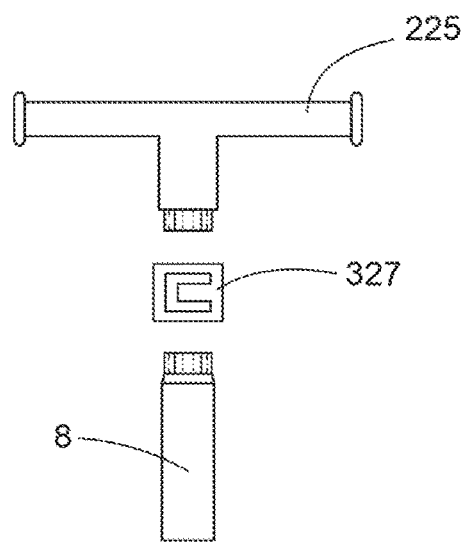

As another example, a torque limiting mechanism or device 327 can be a separate device that is not integrated to handle 25, 125, but can be placed between the handle 25 and set screw driver 26, for example a handle 25 that is not equipped with different types of torque limiting or indicating mechanisms, as shown in FIG. 1E. For example, torque limiting mechanism 327 or device can be embodied to be removable connected to upper shaft 8 or proximal end of set screw driver 26 and handle 25, 125, for example embodied as a mechanical connection element having a ratchet-type or bendable lever or tab that engages with a dented portion, further including two interconnection elements for interconnection between handle 25 and set screw driver 26. In this respect, it is possible to use two different torque limiting mechanisms or devices 327 in this arrangement, one for torque level T1 and one for torque level T2, and the two mechanisms or devices can be visibly marked as such. As another variant, it is possible that the torque limiting or indicating mechanism 27, 127, 327, is part or integrated to upper shaft 8 or proximal end of set screw driver 26, at an area where the handle 225 would be connected to the screw extender 6.

In another variant, it is possible to integrate or connect a torque limiting mechanism or torque indicating mechanism measuring or applying torque limitation between handle 29 and screw extender 6, or by having one torque limiting or torque indicating mechanism measuring or applying torque limitation between handle 29 and screw extender 6, and one torque limiting or torque indicating mechanisms measuring or applying torque limitation between handle 25, 125, 225 and set screw driver 26.

Figure 2A:
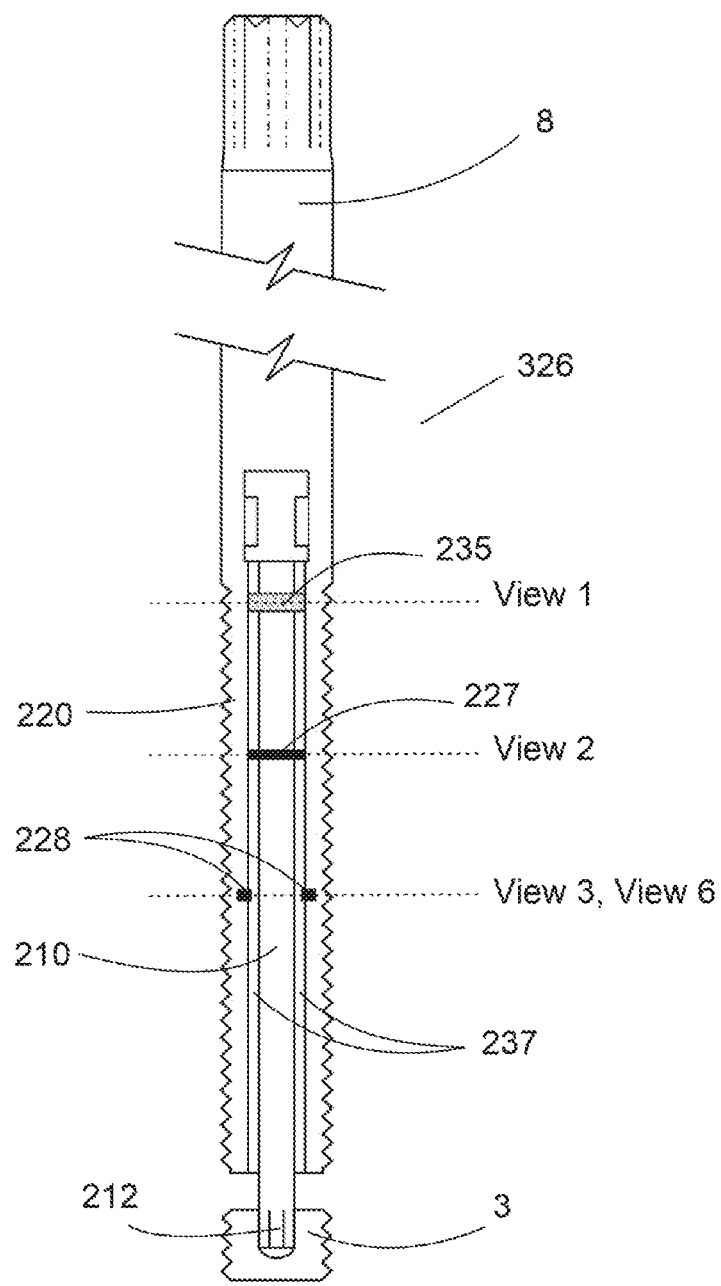
FIGS. 2A to 2E showing different views of a first and second torque limitation feature that is integrated into the set screw driver 226 of an orthopedic tool kit 100, with FIG. 2A showing an exemplary cross-sectional view of set screw driver 226 having a lower section 220 with a hollow cylindrical or tubular body, middle cylindrical shell 237, and a torque driver 210, FIG. 2B showing the first position of blocking bolt 235 with a side view onto middle cylindrical shell 237 with blocking bolt 235, and also showing three cross-sectional views 1, 2, 3 in a direction of center axis of bolt 235, first breakable pin 227, and second breakable pins 228, FIG. 2C showing the second position of blocking bolt 235 with a side view onto middle cylindrical shell 237 with blocking bolt 235, and also showing three cross-sectional views 1, 2, 3 in a direction of center axis of bolt 235, first breakable pin 227, and second breakable pins 228, FIGS. 2D and 2E showing alternative embodiments of bolt 235 that engages with denting showing a side view of an outer surface of middle cylindrical shell 237 and bolt 235.
Figure 2B:
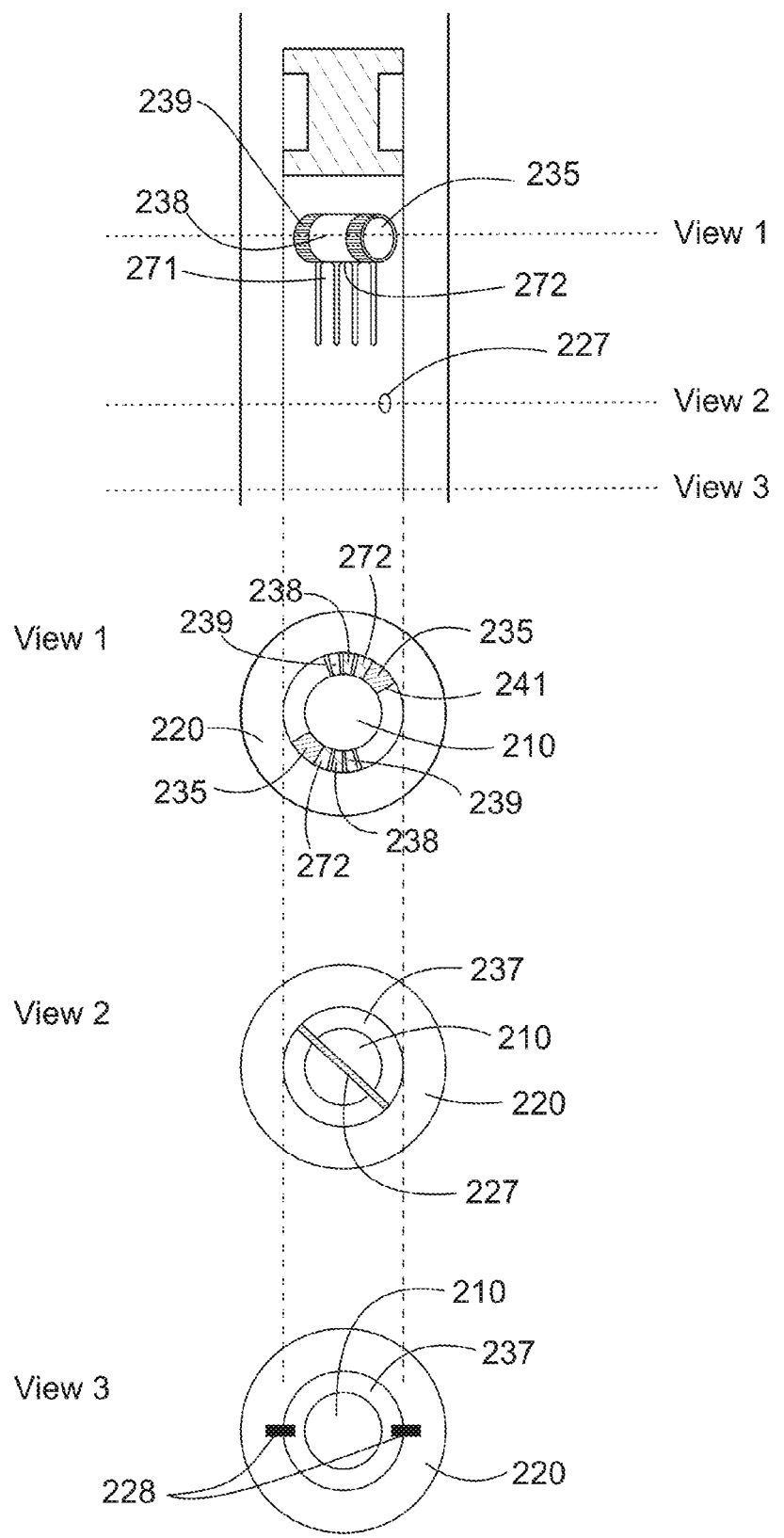
Figure 2C:
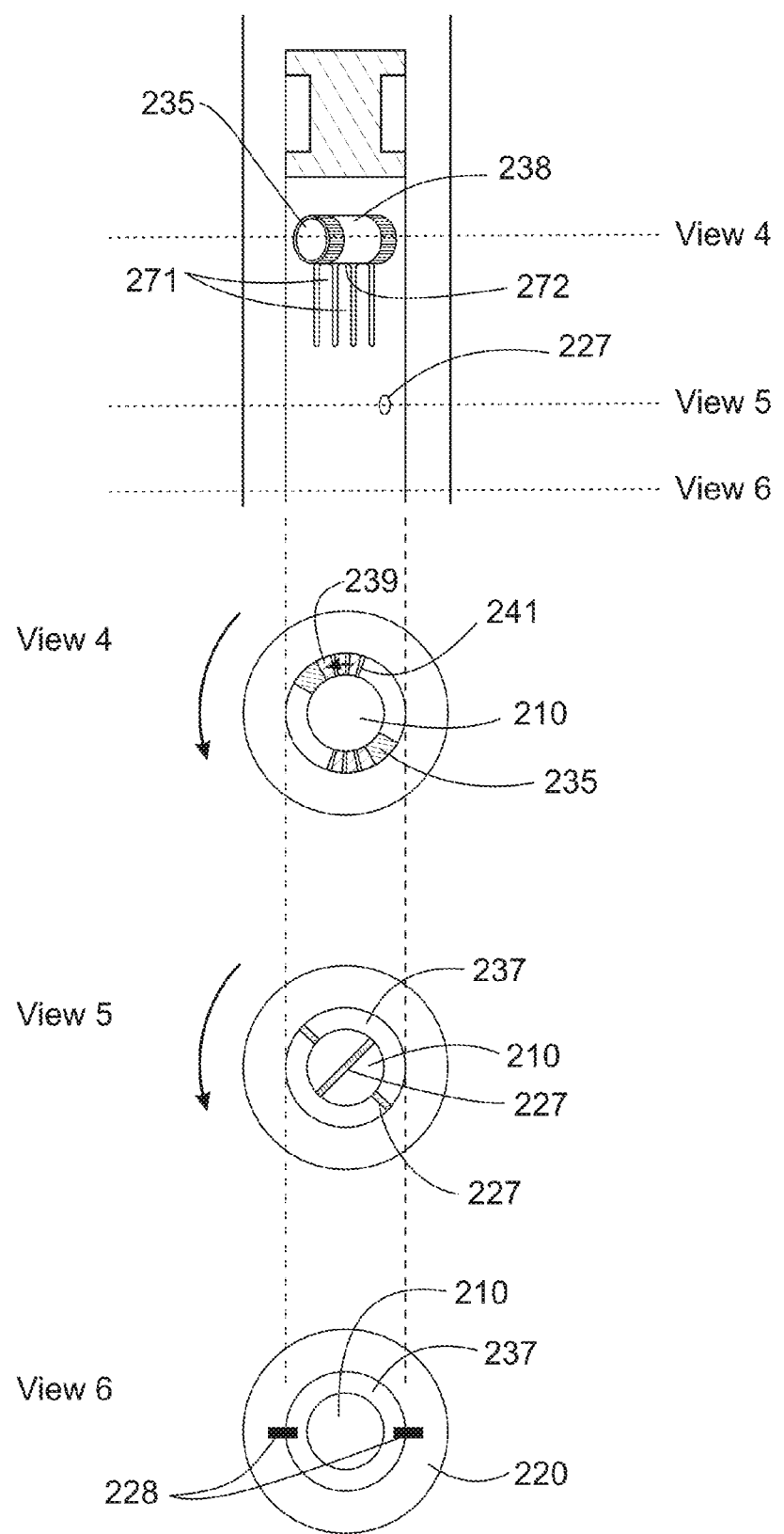

In another variant, as shown in FIGS. 2A-2C, a first torque indicator mechanism is integrated into set screw driver 326 together with the second torque limiting mechanism 228, being a breakable pin. In this variant, set screw driver 326 includes a cylindric hollow area in a lower section 220 that accommodates torque driver 210 having an engagement tool 212 at the distal end for engaging with set screw 3, but also an middle cylindrical shell, tube, or cylinder 237 that is located between lower section 220 of set screw driver and torque driver 210. The first torque indicator mechanism is arrange to mechanically collaborate between torque driver 210 and middle cylindrical shell 237, with a blocking bolt 235 that engages with a transversal slot 238, and a first breakable pin 227 that traverses both torque driver 210 and middle cylindrical shell 237. In a first position, a rotational or turning movement between torque driver 210 and middle cylindrical shell 237 is blocked by first breakable pin 227, limiting the torque that can be applied to a first torque level T1. For this purposes, first breakable pin 227 is dimensioned and designed to break at an application of a torque between torque driver 210 and middle cylindrical shell 237 at the first torque level. In other words, the breaking of pin 227 can be considered the release of a first torque retention mechanism that is embodied by pin 227. In a second position, rotation between torque driver 210 and middle cylindrical shell 237 is again blocked by wall 239 of transversal slot 238.

The first position is represented in FIG. 2B with different cross-sectional views 1, 2, 3 along a center axis of set screw driver 326. Upon application of a low torque below first torque level T1 with set screw driver 326, for example with a handle 125, 225, blocking bolt 235 abuts against side wall 241 of the traversal slot 238, and first breakable pin 227 is not broken yet. Upon exceeding the first torque level T1 between torque driver 210 and middle cylindrical shell 237, first breakable pin 227 will break, as shown in FIG. 2C in cross-sectional view 4. This will create a mechanical jolt or jerk to the set screw driver 326 that can be felt by the user, and will also create a audible click or snap that can be heard by the user, and can serve as a signal to the user that the first torque has been reached, as a first torque indication mechanism. Next, blocking bolt 235 will move from being in contact with side wall 241 and will move through traversal slot 238 to abut and be again blocked by the other side wall 239, to transition from the first position to the second position, by a rotation of a specific angle defined by a length of traversal slot 238 between torque driver 210 and middle cylindrical shell 237, as shown with three cross-sectional views 4, 5, 6 of FIG. 2C representing the second position. Blocking bolt 235 will then abut against one a side wall 241 of the traversal slot 238.

Middle cylindrical shell 237 and lower section 220 of set screw driver 326 are still blocked together with second breakable pin 228 that require a higher, second torque level T2 to break. In this respect, pin 228 can be considered a second torque retention mechanism that holds the two elements 237 and 220 together until the second torque level T2 is reached, and will release upon reaching second torque level T2. In this respect, as an example, one or two (2) or more second breakable pins 228 are arranged at 180 degrees respect to each other to lock a rotation of set screw driver 226 having a lower section 220 relative to middle cylindrical shell 237, up to an application of the higher, second torque level T2. In a variant, there can be several breakable pins 228. For controlled breaking, it is preferable that there is only one second breakable pin 228.

Instead of pins 227, 228, other types of breakable, bendable, releasable, retrainable devices can be used that upon application of a specific torque threshold level can release a rotational blockage between middle cylindrical shell 237 and set screw driver 326 at second torque level T2 to form the second torque retention mechanism, or between torque driver 210 and middle cylindrical shell 237 at first torque level T1 to form the first torque retention mechanism, for example but not limited to breakable plates, breakable hooks, levers, ratchet-type fastening elements that can release upon application of a threshold torque, dented structures.

In addition to the breaking of first breakable pin 227, and the slipping of bolt within transversal slot 238, which results in torque driver 210 turning by a limited angle relative to middle cylindrical shell 237, an additional mechanism can be provided to further alert the user, operator, or surgeon operating the set screw driver 326 that the first torque level has been reached. In the variant shown, during the transition from the first position to the second position by blocking bolt 235, in other words the slipping of bolt 235 from wall 241 to 239 of slot 238, protrusions 272 to lower side wall or upper side wall of transversal slot 238 are made such that the passing of blocking bolt 235 over these protrusions 272 will create a clicking or ratcheting noise, and also depart a vibration that can be heard and felt by the user, operator, or surgeon. In the variant shown, a plurality of thin longitudinal slots 271 are arranged that start from a lower or upper side wall of transversal slot 238, having small protrusions 272 on the top, the protrusions designed to let blocking bolt 235 transition from the first position to the second position with little additional torque, being a torque that is smaller or substantially smaller than the first torque level T1, and thereby making a vibration or ratcheting noise when blocking bolt 235 passes over these protrusions 272.

Figure 2D:
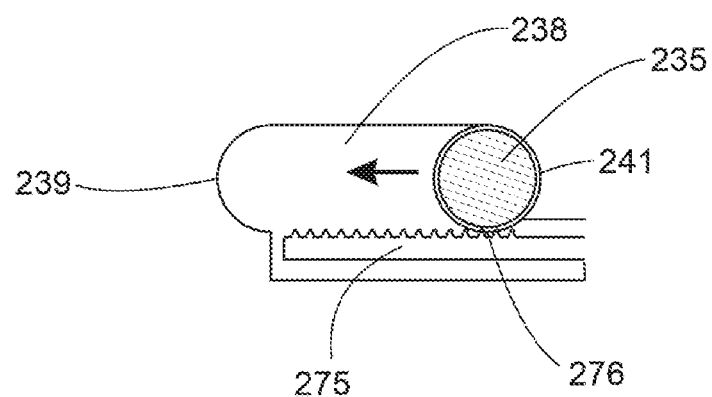
Figure 2E:
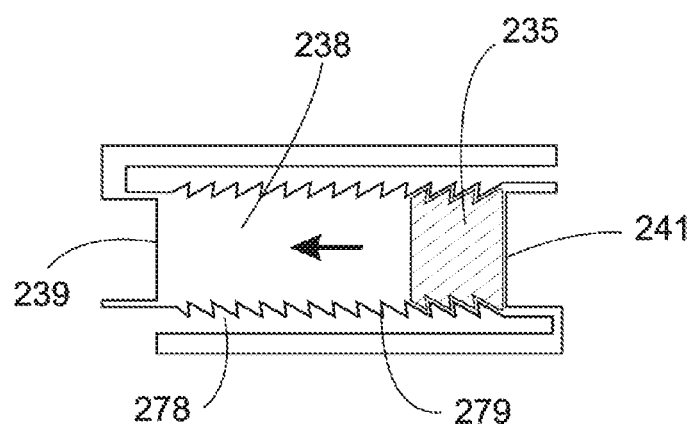

Other mechanism can be used to create an additional indication to the user, operator or surgeon that the first torque level T1 has been reached, for example as shown in FIG. 2D, where a lever 275 having teeth, dents, or arranged in parallel to lateral extension of transversal slot 238 that engages with teeth, dents, cogs, pinions, ratchets 276 of blocking bolt 235, that will create a ratcheting noise and a vibration, upon transition from the first position to the second position. Another example is shown in FIG. 2E, with two levers 278 that are symmetrically arranged on both the upper and lower side of transversal slot 238, with bolt 235 having a square or rectangular cross-section, with the levers 278 having sawtooth shape, to ensure that the transition from the first position to the second position can only happen once and in one direction. The direction of the saw teeth will prevent moving bolt 235 back through transversal slot 238. Instead of levers, it is possible that a portion of middle cylindrical shell 237 has an edge with saw teeth, waves or triangular teeth, and a portion of the bolt 235 has corresponding saw teeth, waves or triangular teeth, respectively that are urged together by a spring mechanism. The biasing force of the spring mechanism that urges the corresponding teeth together can be designed to provide for the first torque level T1.

With the above embodiment, the breaking of first breakable pin 227 or the clicking of bolt 235 against rough, dented, or jagged structures such as lever 275, or protrusions 272, 276, while bolt 235 is transitioning through transversal slot 238, or both of these combined, create an audible, clicking, and vibratory feedback to user, operator, or surgeon that is operating handles 125, 225 and handle 29 to tighten set screw 3 with both of his hands, to reach and exceed first torque level T1, without the need to use different handles or the use of scales with the need of reading a torque level. The breaking of first breakable pin 227 will give a small jolt, clicking, or cracking noise, while the dented structures will depart a vibration and a clicking noise, to make sure that the user will be certain that the first torque level on set screw 3 has been reached. In addition, the dented structures can also provide for mechanical retention against the rotational movement between torque driver 210 and middle cylindrical shell 237, and can serve as torque limiting mechanism for first torque level T1 by themselves.

As of another variant, there is no first breakable pin 227 present, but the protrusions 272 or the lever 275 or a ratchet-like element are designed to block the slipping of blocking bolt 235 within transversal slot 238 to provide for a mechanical retention, upon application of a torque between torque driver 210 and middle cylindrical shell 237, until the first torque level T1 is reached, where bolt 235 moves, transitions, or slips to the side wall 239 of transversal slot 238. Lever 275 and its length and mass, protrusions 272, 276, and longitudinal slots 271 can be designed to depart a specific acoustic sound that is hearable audible by user, surgeon, or operator, when bolt 235 slips through transversal slot 238. Without the first breakable pin 227, it is possible to turn back torque driver 210 relative middle cylindrical shell 237, so that the first position is reached again, to have a reversible mechanism to indicate the first torque level. In this respect, the first torque limiting mechanism and the first torque indicating mechanism could be integrated into a common arrangement, for example by a ratchet-type arrangement with one or more dents engaging with a sawtooth or waved structure, as described above.

In the context of the present invention, with the first breakable pin 227 and the other types of retention mechanisms shown in FIGS. 2B and 2C with longitudinal slots 271 and protrusions 272, or in FIGS. 2D and 2E with levers 275 and protrusions 272, 276, 279, different arrangements are described that are herein called a first torque retention mechanism, that can serve as an indicator when the first torque has been surpassed or reached, or as a torque limiter to limit application of the first torque to the first torque level, or both.

Figure 3A:
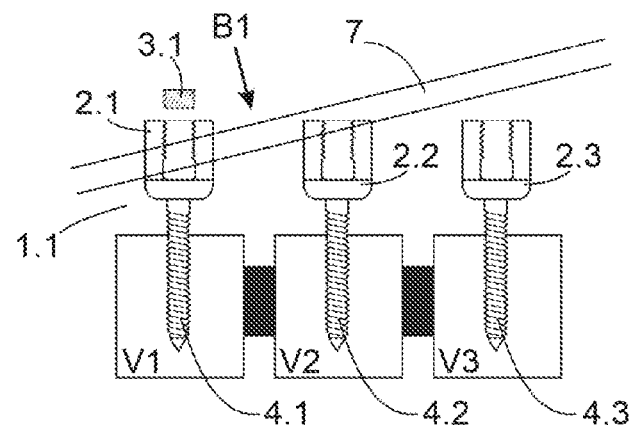
FIGS. 3A to 3E showing exemplary cross-sectional views of different stages of a method during a spinal stabilization surgical procedure, according to another aspect of the present invention.

According to another aspect, a method of placing a spinal rod 7 into a series of heads 2 of pedicle screws 1 and the tightening or fastening of set screws 3 to these heads is provided, as illustrated in FIGS. 3A to 3E. In these figures, showing different stages of the method, by an example showing three pedicle screws 1.1 to 1.3 attached to three vertebrae V1 to V3, but it is also within the scope of this embodiment that a different number of pedicle screws 1.1 to 1.3 and a different number of vertebrae V1 to V3 are used. These figures schematically and exemplarily show three adjacent vertebrae V1 to V3, each having a pedicle screw 1.1, 1.2, and 1.3, respectively, attached thereto, with respective bone anchor 4.1, 4.2, and 4.3. Before what is shown in FIG. 3A, none of the screw heads 2.1, 2.2, and 2.3 of pedicle screws 1.1, 1.2, and 1.3 have spinal rod 7 inserted therein. As shown in FIG. 3A, user starts by placing the left side of spinal rod 7 into screw head 2.1 by moving spinal rod 7 in direction B1 such that rod 7 is placed into U-shaped groove of head 2.1, and then threadably but loosely attaches a set screw 3.1 to screw head 2.1, to make sure that rod 7 does not exit U-shaped groove of screw head 2.1. Generally, spinal rod 7 will have a pre-bent shape that will be desired shape of the spinal column for fusion, so that adjacent vertebrae V1 to V3 will be urged to a desired arrangement next to each other by spinal rod 7.

Figure 3B:
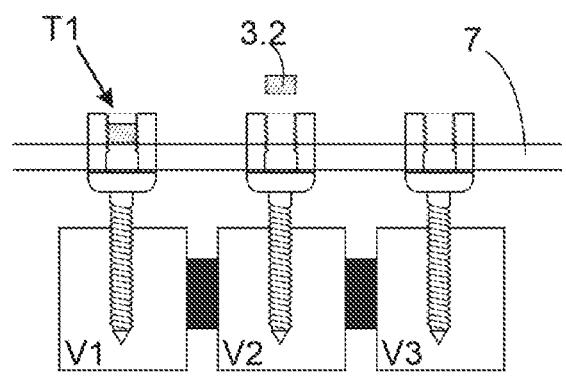
Figure 3C:
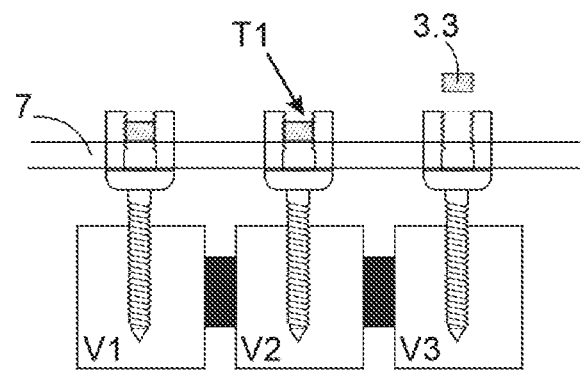

Next, as illustrated in FIG. 3B, set screw 3.1 is threaded down into screw head 2.1 to abut against rod 7 and is threadably attached to head 2.1 by first torque level T1, by using the instruments or tool kit 100 as described above, and at this time, the pre-bent rod 7 lies inside the U-shaped grooves of both adjacent heads 2.2 and 2.3. After this, user threadably but loosely attaches a set screw 3.2 to screw head 2.2. Next, as illustrated in FIG. 3C, set screw 3.2 is threaded down into screw head 2.2 to abut against rod 7 and is threadably attached to head 2.2 by first torque level T1, again by using the instruments or tool kit 100 as described above. After this, user threadably but loosely attaches a set screw 3.3 to screw head 2.3.

Figure 3D:
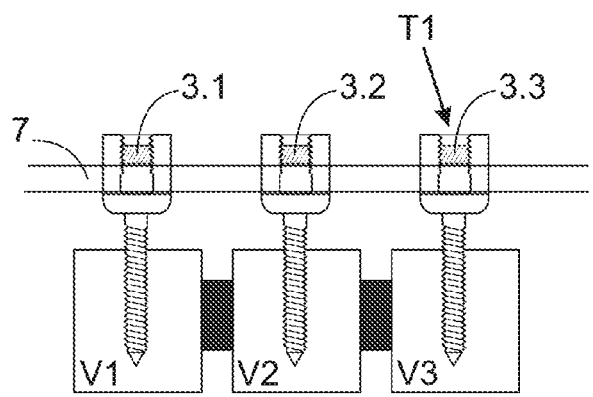
Figure 3E:
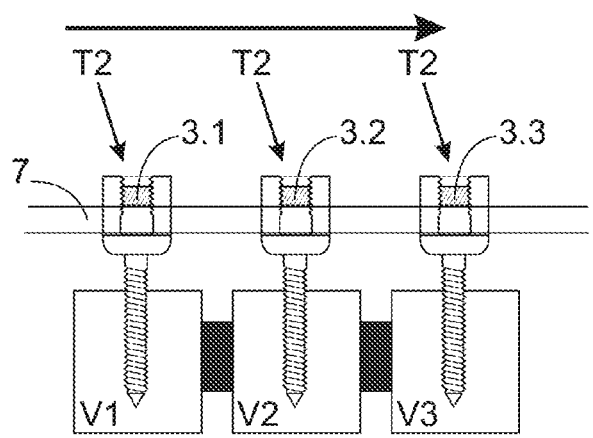

Thereafter, as shown in FIG. 3D, set screw 3.3 is threaded down into screw head 2.3 to abut against rod 7 and is threadably attached to head 2.3 by first torque level T1, again by using the instruments or tool kit 100. At this stage, all the pedicle screws 1.1, 1.2, and 1.3 are attached to rod 7, by set screws 3.1 to 3.3 that are tightening by a torque at the first torque level T1. Next, as shown in FIG. 3E, starting from the left side to the right, each set screw 3.1, 3.2, and 3.3 is tightened at the second torque level T2, to finalize the spinal stabilization with spinal rod 7. This is done by using the second torque limiting feature of tool kit 100. For each set screw 3.1, 3.2, and 3.3, a different tool kit 100 is used. Generally, as the spinal rod 7 has a pre-bent shape, spinal rod 7 can be placed into two or more pedicle screw heads at once, and the sets screws 3.1 to 3.3 are thereafter tightening one-by-one in series, from either direction along spinal rod 7. With this method, it is possible to reduce the tightening steps into a single instrument kit, even to a single instrument itself as described above, permitting substantial operation time savings and costs.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. An orthopedic implant kit for tightening a set screw to a head of a pedicle screw, the kit comprising:
   a screw extender configured to hold the head of the pedicle screw, the screw extender including an inner threading;
   a set screw driver configured to engage with the set screw to threadably tighten the set screw relative to the head of the pedicle screw, the set screw driver including an outer threading configured to threadably engage with the inner threading of the screw extender to turn or rotate the set screw together with the set screw driver through the screw extender;
   a first torque limiting mechanism configured to limit a torque between the set screw driver and the screw extender to a first torque value, or a first torque indication mechanism configured to indicate that the first torque value has been reached between the set screw driver and the screw extender; and a second torque limiting mechanism configured to limit a torque between the set screw driver and the screw extender to a second torque value, the second torque value being higher than the first torque value.

2. The orthopedic implant kit according to claim 1, wherein the first torque limiting mechanism or the first torque indication mechanism and the second torque limiting mechanism are integrated into the set screw driver.

3. The orthopedic implant kit according to claim 2, wherein the set screw driver comprises:
a shaft having a set screw engagement portion,
a tubular element surrounding the shaft, and
an outer shell surrounding the tubular element, the outer shell having the outer threading configured to threadably engage with the inner threading of the screw extender,
wherein a first breakable pin is disposed between the tubular element and the outer shell forming a part of the first torque limiting mechanism or the first torque indication mechanism, and a second breakable pin is disposed between the tubular element and the shaft forming the second torque limiting mechanism.

4. The orthopedic implant kit according to claim 3, wherein the set screw driver further includes:
a mechanism configured to generate at least one of a vibration or a noise upon breaking of the first breakable pin as a part of the first torque indicating mechanism.

5. The orthopedic implant kit according to claim 4, wherein the mechanism includes a protrusion that engages with a dented portion of a side wall of the tubular element.

6. The orthopedic implant kit according to claim 3, wherein the set screw driver further includes:
a bolt configured to block a rotational movement between the tubular element and the outer shell after the first breakable pin is broken.

7. The orthopedic implant kit according to claim 2, wherein the set screw driver comprises:
a shaft having a set screw engagement portion,
a tubular element surrounding the shaft, and
an outer shell surrounding the tubular element, the outer shell having the outer threading configured to threadably engage with the inner threading of the screw extender,
wherein a first release device configured to release a rotational blockage is disposed between the tubular element and the shaft forming a part of the first torque limiting mechanism or the first torque indication mechanism, and a second release device configured to release a rotational blockage is disposed between the tubular element and the outer shell forming the second torque limiting mechanism.

8. The orthopedic implant kit according to claim 1, further comprising:
a handle configured to turn the set screw driver relative to the screw extender, the first torque limiting mechanism or the first torque indication mechanism arranged disposed between the handle and the set screw driver, and the second torque limiting mechanism integrated into the set screw driver.

9. The orthopedic implant kit according to claim 1, further comprising:
a handle configured to turn the set screw driver relative to the screw extender, the first torque limiting mechanism or the first torque indication mechanism configured to be disposed between the handle and the set screw driver, and the second torque limiting mechanism configured to be disposed between the handle and the set screw driver.

10. The orthopedic implant kit according to claim 1, wherein the first torque indication mechanism includes at least one of a torque scale, a mechanism that generates a vibration upon passing the first torque value, a mechanism that generates a jolt upon passing the first torque value, and a mechanism that generates an audible noise upon passing the first torque value.

11. The orthopedic implant kit according to claim 1, wherein the outer threading of the set screw driver has a same thread pitch as a threading of the set screw to turn or rotate the set screw together with the set screw driver through the screw extender.

12. The orthopedic implant kit according to claim 1, wherein the set screw and the set screw driver are configured to be threadably rotated through the inner threading of the screw extender.

13. The orthopedic implant kit according to claim 1, wherein the inner threading of the screw extended is disposed at least at a distal end of the screw extender, and the outer threading of the set screw driver is disposed at least at a distal end of the set screw driver.

14. The orthopedic implant kit according to claim 1, wherein the first torque limiting mechanism or the first torque indication mechanism is operatively connected to the set screw driver at a different location to a location of the second torque limiting mechanism, and
the set screw driver includes an upper shaft configured to engage with a handle and a hollow lower shaft accommodating a torque driver inside the hollow lower shaft, the torque driver comprising a screw engagement mechanism disposed at a distal end of the torque driver, the screw engagement mechanism being configured to engage with the set screw, the second torque limiting mechanism being integrated into the hollow lower shaft.

15. A set screw driver for an orthopedic implant kit having a screw extender for tightening a set screw to a head of a pedicle screw, the set screw driver comprising:
a first torque limiting mechanism for limiting a torque between the set screw driver and the screw extender to a first torque value, or a first torque indication mechanism for indicating that the first torque value has been reached between the set screw driver and the screw extender;
a second torque limiting mechanism for limiting a torque between the set screw driver and the screw extender to a second torque value, the second torque value being higher than the first torque value; and
an outer threading configured to threadably engage with inner threading of the screw extender to turn or rotate the set screw together with the set screw driver through the screw extender.

16. The set screw driver according to claim 15, further comprising:
a shaft having a set screw engagement portion;
a tubular element surrounding the shaft; and
an outer shell surrounding the tubular element,
wherein a breakable pin or a ratchet-type device is arranged between the tubular element and the outer shell forming a part of the first torque limiting mechanism or first torque indicating mechanism, and a second breakable pin is arranged between the tubular element and the shaft forming the second torque limiting mechanism.

17. The set screw driver according to claim 16, wherein the set screw driver further includes:
   a bolt for blocking a rotational movement between the tubular element and the outer shell after the breakable pin breaks or a ratchet-type device releases.

18. The set screw driver according to claim 15, wherein the first torque indication mechanism includes at least one of a mechanism that generates a vibration upon passing the first torque value, a mechanism that generates a jolt upon passing the first torque value, and a mechanism that generates an audible noise upon passing the first torque value.

* * * * *